United States Patent
Engelbart et al.

(10) Patent No.: US 9,038,470 B1
(45) Date of Patent: May 26, 2015

(54) POROSITY INSPECTION SYSTEM FOR COMPOSITE STRUCTURES

(75) Inventors: Roger W. Engelbart, St. Louis, MO (US); Christopher M. Vaccaro, O'Fallon, MO (US); Scott E. Black, Godfrey, IL (US); Nancy Wood, Clayton, MO (US)

(73) Assignee: THE BOEING COMPANY, Chicago, IL (US)

( * ) Notice: Subject to any disclaimer, the term of this patent is extended or adjusted under 35 U.S.C. 154(b) by 382 days.

(21) Appl. No.: 13/568,985

(22) Filed: Aug. 7, 2012

(51) Int. Cl.
*G01N 29/04* (2006.01)
*G01N 29/11* (2006.01)
*G01N 15/08* (2006.01)

(52) U.S. Cl.
CPC .................................. *G01N 29/04* (2013.01)

(58) Field of Classification Search
CPC ....... G01N 29/11; G01N 15/08; G01N 29/04; G01N 2291/0231; G01N 29/043; G01N 29/0289
USPC ............................. 73/599, 627, 628, 629, 602
See application file for complete search history.

(56) References Cited

U.S. PATENT DOCUMENTS

| | | | |
|---|---|---|---|
| 7,353,709 B2 | 4/2008 | Kruger et al. | |
| 7,362,427 B2 | 4/2008 | Fayolle et al. | |
| 7,362,437 B2 * | 4/2008 | Engelbart et al. | 356/430 |
| 7,389,693 B2 * | 6/2008 | Reed et al. | 73/629 |
| 7,762,120 B2 | 7/2010 | Vaccaro et al. | |
| 8,826,740 B2 * | 9/2014 | Bergman | 73/602 |
| 2007/0006651 A1 | 1/2007 | Kruger et al. | |

FOREIGN PATENT DOCUMENTS

EP 2487487 A1 8/2012

OTHER PUBLICATIONS

Englebart et al., "Porosity Inspection System for Composite Structures with Non-Parallel Surfaces," U.S. Appl. No. 13/897,007, filed May 17, 2013, 50 pages.
International Search Report and Written Opinion, dated Aug. 4, 2014, regarding Application No. PCT/US2014/034637, 10 pages.
Hsu et al., "Simultaneous ultrasonic velocity and sample thickness measurement and application in composites," The Journal of the Acoustical Society of America, vol. 92, No. 2, Aug. 1992, pp. 669-675.

* cited by examiner

*Primary Examiner* — J M Saint Surin
(74) *Attorney, Agent, or Firm* — Yee & Associates, P.C.

(57) ABSTRACT

A method and apparatus for inspecting a composite structure. A response sound signal to a sound signal sent into the composite structure at a location on the composite structure is detected. An attenuation is identified in the response sound signal detected in response to the sound signal sent into the composite structure at the location on the composite structure. An indication of whether additional evaluation of the location is needed based on a comparison of the attenuation in the response sound signal to a baseline attenuation value for porosity for the location on the composite structure is generated.

29 Claims, 12 Drawing Sheets

POROSITY INSPECTION SYSTEM FOR COMPOSITE STRUCTURES

BACKGROUND INFORMATION

1. Field

The present disclosure relates generally to composite structures and, in particular, to inspecting composite structures. Still more particularly, the present disclosure relates to a method and apparatus for inspecting composite structures to identify porosity in the composite structures.

2. Background

Aircraft are being designed and manufactured with greater and greater percentages of composite materials. Composite materials are used in aircraft to decrease the weight of the aircraft. This decreased weight improves performance features such as payload capacity and fuel efficiency. Further, composite materials provide longer service life for various components in an aircraft.

Composite materials may be tough, light-weight materials created by combining two or more functional components. For example, a composite material may include reinforcing fibers bound in a polymer resin matrix. The fibers may be unidirectional or may take the form of a woven cloth or fabric. The fibers and resins may be arranged and cured to form a composite structure.

Using composite materials to create aerospace composite structures may allow for portions of an aircraft to be manufactured in larger pieces or sections. For example, a fuselage in an aircraft may be created in cylindrical sections to form the fuselage of the aircraft. Other examples include, without limitation, wing sections joined to form a wing or stabilizer sections joined to form a stabilizer.

In manufacturing composite structures, layers of composite material may be laid up on a tool. The layers of composite material may be comprised of fibers in sheets. These sheets may take the form of, for example, without limitation, fabrics, tape, tows, or other suitable configurations for the sheets. In some cases, resin may be infused or pre-impregnated into the sheets. These types of sheets are commonly referred to as prepreg.

The different layers of prepreg may be laid up in different orientations and different numbers of layers may be used depending on the desired thickness of the composite structure being manufactured. These layers may be laid up by hand or using automated lamination equipment such as a tape laminating machine or a fiber placement system.

After the different layers have been laid up on the tool, the layers may be consolidated and cured upon exposure to temperature and pressure, thus forming the final composite structure. Thereafter, the composite structure may be inspected to determine whether inconsistencies are present. The inspection may be performed using ultrasound testing, infrared testing, visual inspections, and other suitable types of testing.

This testing may be performed to identify various inconsistencies in the composite structure. For example, inconsistencies may include delamination, voids, undesired levels of porosity, and other types of inconsistencies.

With respect to porosity levels, increasing porosity in a composite structure may result in less than desired load that the composite structure is able to withstand and perform as desired. Thus, a composite structure may be inspected using ultrasound testing to determine whether the porosity level is within a desired level for the composite structure.

Currently, when ultrasound testing is used to determine the porosity of the composite structure, the entire surface of the composite structure may be inspected. For example, an ultrasound system may perform ultrasound testing to gather data from all of the surfaces of each composite structure. This data may then be analyzed by an operator to identify the porosity of the composite structure. This inspection of the entire surface of the composite structure may take more time and manpower than desired.

Further, the analysis of the data may add to the time and manpower needed to inspect these composite structures. As a result, ultrasound testing of composite structures may take more time and may cost more than desired. Therefore, it would be desirable to have a method and apparatus that takes into account at least some of the issues discussed above, as well as possibly other issues.

SUMMARY

In one illustrative embodiment, a method for inspecting a composite structure is present. A response sound signal to a sound signal sent into the composite structure at a location on the composite structure may be detected. An attenuation may be identified in the response sound signal detected in response to the sound signal sent into the composite structure at the location on the composite structure. An indication of whether additional evaluation of the location is needed based on a comparison of the attenuation in the response sound signal to a baseline attenuation value for porosity for the location on the composite structure may be generated.

In another illustrative embodiment, a method for inspecting a composite structure is present. A sound signal may be sent into the composite structure a location on the composite structure. A response sound signal to the sound signal sent into the composite structure at the location on the composite structure may be detected. An attenuation may be identified in the response sound signal detected in response to the sound signal sent into the composite structure at the location. A baseline attenuation value for porosity at the location on the composite structure may be identified. The attenuation of the response sound signal may be compared with the baseline attenuation value for porosity for the location on the composite structure to form a comparison. An indication of whether additional evaluation of the location is needed based on the comparison of the attenuation in the response sound signal to the baseline attenuation value for porosity for the location on the composite structure may be generated. The sending step, the detecting step, the identifying steps, and the generating step may be performed for locations on the composite structure to form a number of indications of whether additional evaluation of the locations is needed. A number of images of the composite structure may be generated. A set of graphical indicators on the number of images in areas corresponding to a set of areas on the composite structure needing the additional evaluation using the number of indications may be associated to generate a map of areas on the composite structure needing the additional evaluation using the number of indications.

In yet another illustrative embodiment, an apparatus may comprise an analyzer. The analyzer may be configured to identify an attenuation in a response sound signal detected in response to a sound signal sent into a composite structure at a location. The analyzer may be further configured to generate an indication of whether additional evaluation of the location is needed based on a comparison of the attenuation in the response sound signal to a baseline attenuation value for porosity for the location on the composite structure.

In still yet another illustrative embodiment, an ultrasound inspection system for a composite structure may comprise a number of transducers and an analyzer. The number of transducers may be configured to send sound signals into the composite structure. The number of transducers may be further configured to detect response sound signals to the sound signals sent into the composite structure. The analyzer may be configured to detect the response sound signals to the sound signals sent into the composite structure at locations on the composite structure. The analyzer may be further configured to identify attenuations in the response sound signals detected in response to the sound signals sent into the composite structure at the locations. The analyzer may be further configured to identify baseline attenuation values for porosity at the locations on the composite structure. The analyzer may be further configured to compare the attenuations of the response sound signals with the baseline attenuation values for porosity for the locations on the composite structure to form comparisons. The analyzer may be further configured to generate a number of indications of whether additional evaluations of the locations are needed based on the comparisons of the attenuations in the response sound signals to the baseline attenuation values for porosity for the locations on the composite structure. The analyzer may be further configured to generate a number of images of the composite structure. The analyzer may be further configured to associate a set of graphical indicators on the number of images in areas corresponding to a set of areas on the composite structure needing the additional evaluations using the number of indications to form a map of areas on the composite structure needing the additional evaluations using the number of indications.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account one or more different considerations. For example, the illustrative embodiments recognize and take into account that when evaluating the level of porosity in a composite structure, an operator may compare the attenuation of the composite structure that is under test to a baseline attenuation for a desired level porosity for the composite structure.

In performing this comparison, the data from the ultrasound testing may be presented using images of the composite structure in which the level of porosity may be displayed using a grayscale. For example, the level of porosity of the composite structure may be indicated by the darkness of each representative area within the grayscale image of the composite structure. However, the actual value of the level of porosity may be more difficult to identify than desired from the level of darkness in a representative area. With currently used evaluation methods, the operator may maneuver through a variety of system tools to conduct the evaluation based on the gray areas indicated in the test data. This evaluation may be repeated for each thickness of each part over the entire surface of the aircraft. Conducting an evaluation of each thickness of each part of the composite structure may take more time than desired.

Moreover, the illustrative embodiments recognize and take into account that after the analysis of the original data is completed, the operator may perform additional testing in some areas of the composite structure to obtain more detailed information about the porosity of that composite structure.

For example, some areas of the composite structure may appear to have disbonding and/or delamination. In this instance, heavier levels of porosity than desired may be seen in the original test data. With potential areas of disbonding and/or delamination, additional ultrasound testing may be performed on a composite structure using a different transducer or different frequency of the transducer used during the first test. In this case, additional analysis of test data may be performed.

This additional analysis of the data may be more time-consuming and tedious than desired. Consequently, the manufacturing and testing of composite structures may be more expensive and less efficient than desired.

Thus, in one illustrative embodiment, a composite structure may be inspected by detecting a response sound signal to a sound signal sent into the composite structure at a location on the composite structure. An attenuation in the response sound signal detected in response to the sound signal sent into the composite structure at the location may be identified. An indication of whether additional evaluation of the location is needed may be generated based on a comparison of the attenuation in the response to a baseline attenuation value for porosity for a thickness of the location on the composite structure.

Figure 1:
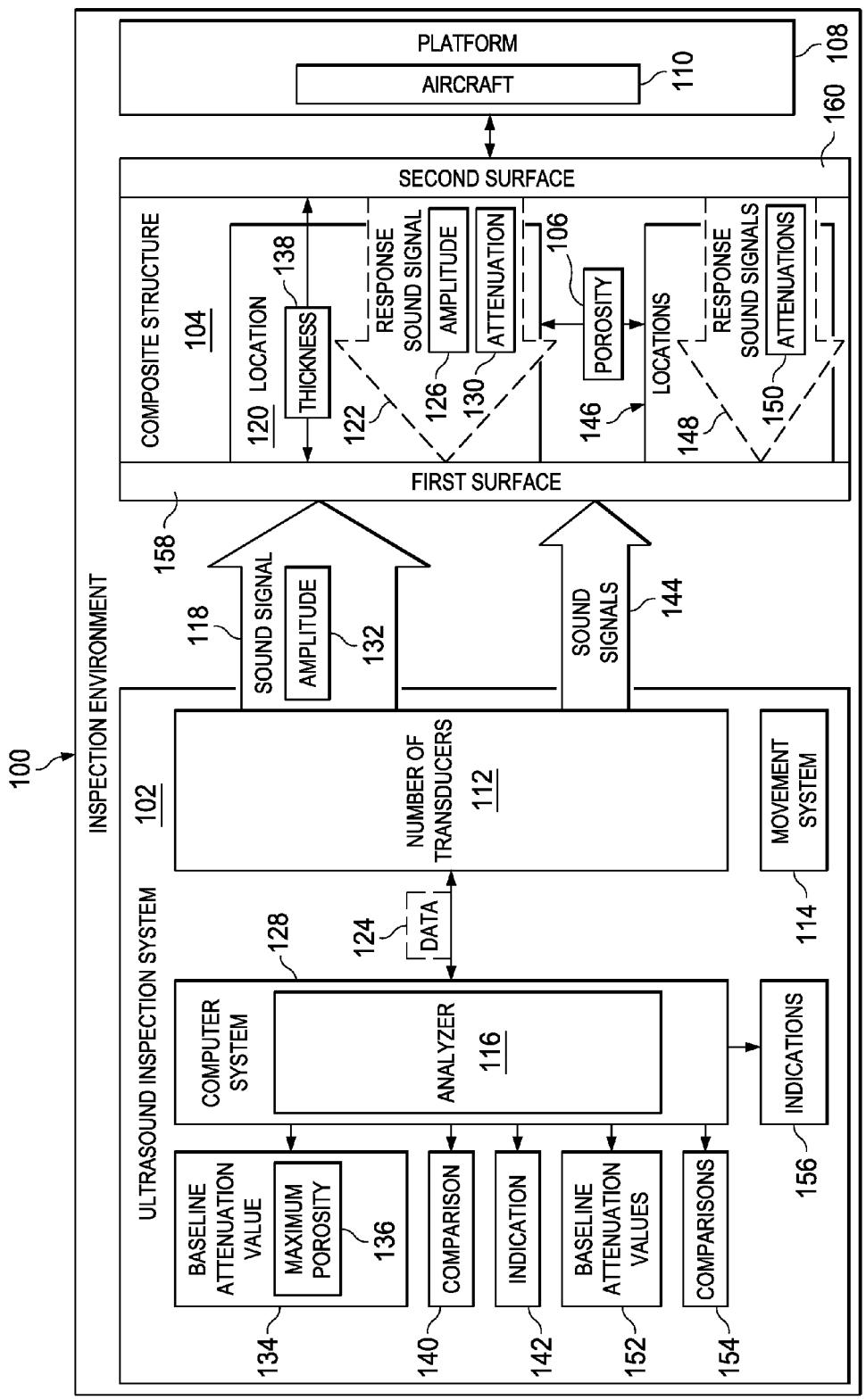
FIG. 1 is an illustration of a block diagram of an inspection environment in accordance with an illustrative embodiment.

With reference now to the figures and, in particular, with reference to FIG. 1, an illustration of a block diagram of an inspection environment is depicted in accordance with an illustrative embodiment. In this depicted example, inspection environment 100 includes ultrasound inspection system 102. Ultrasound inspection system 102 may be used to perform an inspection of composite structure 104. In particular, an inspection may be conducted to determine porosity 106 in composite structure 104.

In this illustrative example, composite structure 104 may be part of platform 108. As depicted, platform 108 may take a number of different forms. In particular, platform 108 may take the form of aircraft 110. Composite structure 104 in aircraft 110 may be, for example, without limitation, one of a skin panel, a fuselage barrel, a stringer, a panel, a flap, a door, a wing box, or some other suitable type of composite structure.

As depicted, ultrasound inspection system 102 may be comprised of number of transducers 112, movement system 114, analyzer 116, and other suitable components. Of course, ultrasound inspection system 102 may include other components not show in this depicted example.

In this illustrative example, number of transducers 112 may be configured to send sound signal 118 into composite structure 104 at location 120. A "number," as used herein with reference to items, means one or more items. For example, number of transducers 112 may be one or more transducers.

Sound signal 118 may be generated by number of transducers 112 under the control of analyzer 116 in this illustrative example. Sound signal 118 may have different frequencies. As depicted, sound signal 118 may be, for example, an ultrasound signal. Without limitation, sound signal 118 may have a frequency from about 20 kilohertz to about 200 megahertz. Of course, other frequencies may be used for sound signal 118 depending on the particular implementation.

In response to sound signal 118 traveling into composite structure 104 at location 120, response sound signal 122 may be generated. In this illustrative example, response sound signal 122 may be detected by number of transducers 112. In response to detecting response sound signal 122, number of transducers 112 may generate and send data 124 to analyzer 116 for processing. Data 124 may be, for example, an electrical signal indicating amplitude 126 of response sound signal 122.

In this illustrative example, analyzer 116 may be implemented using hardware, software, or a combination of the two. When software is used, the operations performed by analyzer 116 may be implemented in program code configured to be run on a processor unit. When hardware is employed, the hardware may include circuits that operate to perform operations in analyzer 116.

The hardware may take the form of a circuit system, an integrated circuit, an application specific integrated circuit (ASIC), a programmable logic device, or some other suitable type of hardware configured to perform a number of operations. With a programmable logic device, the device may be configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. Additionally, the processes may be implemented in organic components integrated with inorganic components and/or may be comprised entirely of organic components excluding a human being. For example, the processes may be implemented as circuits in organic semiconductors.

In this illustrative example, analyzer 116 may be implemented in computer system 128. Computer system 128 may be one or more computers. When more than computer is present in computer system 128, those computers may be in communication with each other via a communication medium such as a network.

In this illustrative example, analyzer 116 may identify attenuation 130 of response sound signal 122. Attenuation 130 may be identified by comparing amplitude 126 of response sound signal 122 with amplitude 132 of sound signal 118.

Analyzer 116 may compare attenuation 130 with baseline attenuation value 134 to identify porosity 106 in composite structure 104 at location 120. Baseline attenuation value 134 represents maximum porosity 136 that is desired for thickness 138 of composite structure 104 at location 120. In this illustrative example, thickness 138 may be a distance from first surface 158 to second surface 160. Location 120 where sound signal 118 enters composite structure 104 may be located on first surface 158. Second surface 160 may be substantially opposite to first surface 158. In these illustrative examples, baseline attenuation value 134 may be identified in a number of different ways. For example, baseline attenuation value 134 may be a baseline value taken for a thickness of a test object that may be a reference standard, a requirements value, a value from a database, or some other suitable type of value for baseline attenuation value 134. As depicted, baseline attenuation value 134 may be a threshold value.

Comparing attenuation 130 of response sound signal 122 to baseline attenuation value 134 may result in comparison 140. If attenuation 130 is greater than baseline attenuation value 134, then porosity 106 at location 120 may be greater than desired. As a result, additional evaluation of location 120 may be needed.

In this illustrative example, indication 142 may be generated by analyzer 116. Indication 142 may be generated based on comparison 140 of attenuation 130 in response sound signal 122 and baseline attenuation value 134 for porosity 106 for thickness 138 of location 120 of composite structure 104.

Indication 142 may indicate whether additional evaluation of composite structure 104 may be needed at location 120. Indication 142 may indicate that additional evaluation of composite structure 104 may be needed at location 120 or that additional evaluation of composite structure 104 may not be needed at location 120.

Further, analyzer 116 may control number of transducers 112 to send sound signals 144 into locations 146 in composite structure 104. As depicted, analyzer 116 may control movement system 114 to move number of transducers 112 with respect to composite structure 104 to locations 146 on at least one of first surface 158 and second surface 160. Number of transducers 112 may then send sound signals 144 into locations 146 on composite structure 104. In this manner, ultrasound inspection system 102 may test all of composite structure 104.

In response to sound signals 144 being sent into locations 146, response sound signals 148 may be generated. Number of transducers 112 may detect response sound signals 148 and generate data 124 about response sound signals 148.

Analyzer 116 may receive data 124 about response sound signals 148 from number of transducers 112 and identify attenuations 150 for response sound signals 148. Analyzer 116 may compare attenuations 150 with baseline attenuation values 152 to form comparisons 154. Based on comparisons 154 of attenuations 150 with baseline attenuation values 152, analyzer 116 may generate indications 156 that indicate whether additional evaluations of locations 146 are needed at locations 146.

These additional evaluations may be additional evaluations for areas of composite structure 104 that may show disbonding or delamination. When disbonding and/or delamination may be present, indications 156 may show heavier levels of porosity than desired. In this illustrative example, these areas of porosity, indicated by indications 156, may be retested.

In other illustrative examples, additional ultrasound testing may be performed on composite structure 104 using a different transducer in number of transducers 112 than was used to send sound signal 118 into composite structure 104 during the first test. Further, areas of composite structure 104 may be retested using a different frequency from number of transducers 112. In this manner, ultrasound inspection system 102 and/or other types of inspection systems may be used to further inspect areas of composite structure 104.

Thus, the illustrative embodiments provide a method to identify the porosity of a composite structure using ultrasound inspection system 102. With the comparison of attenuation 130 to response sound signal 122 and baseline attenuation value 134, an operator may use the illustrative embodiments to quickly and efficiently determine porosity 106 of composite structure 104.

Figure 2:
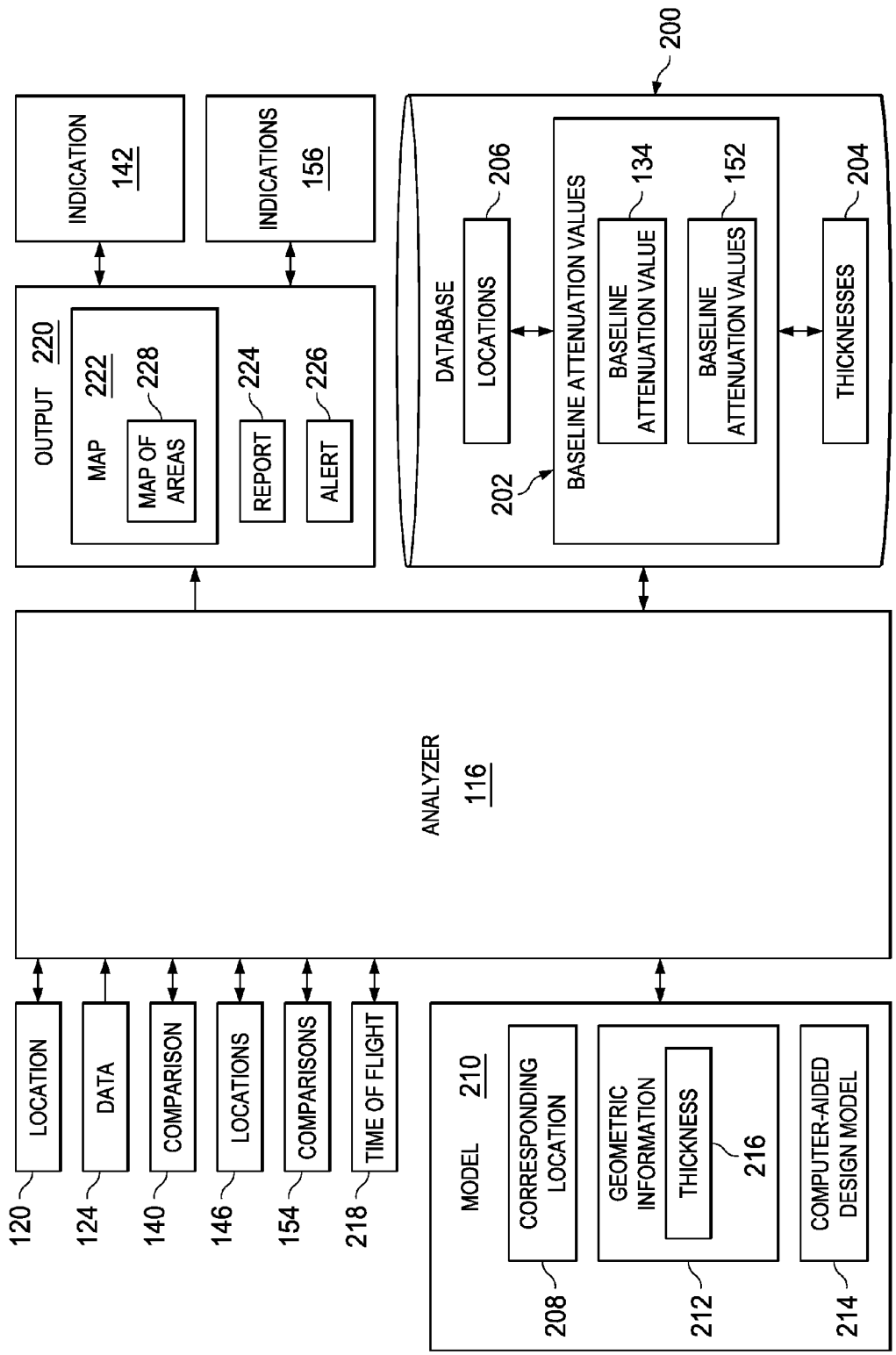
FIG. 2 is a detailed illustration of data flow in an analysis of data for response sound signals in accordance with an illustrative embodiment.

Turning now to FIG. 2, a detailed illustration of data flow in an analysis of data for response sound signals is depicted in accordance with an illustrative embodiment. As depicted, analyzer 116 receives data 124 about response sound signal 122 generated in response to sound signal 118 being sent into composite structure 104 at location 120 as shown in FIG. 1. Data 124 may be used to identify attenuation 130 in response sound signal 122 as shown in FIG. 1.

With attenuation 130, database 200 may be used to identify baseline attenuation value 134 from baseline attenuation values 202. In these illustrative examples, baseline attenuation values 202 may be indexed in a number of different ways. For example, at least one of thicknesses 204 and locations 206 may be used as an index in baseline attenuation values 202. Thicknesses 204 and locations 206 may correspond to thicknesses and locations in composite structure 104 in FIG. 1.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C, or item B and item C. In other examples, "at least one of" may be, for example, without limitation, two of item A, one of item B, and ten of item C; four of item B and seven of item C; and other suitable combinations.

In one illustrative example, location 120 where sound signal 118 was sent into composite structure 104 as shown in FIG. 1 may be used by analyzer 116 to identify baseline attenuation value 134 in baseline attenuation values 202. More specifically, analyzer 116 may use locations 120 as an index to identify baseline attenuation value 134 that corresponds to location 120 in locations 206 in database 200.

In another illustrative example, analyzer 116 also may use thickness 138 of composite structure 104 at location 120 as shown in FIG. 1 as an index to identify baseline attenuation value 134 that corresponds to thickness 138 in thicknesses 204 in database 200. In other words, thicknesses 204 serves as an index to identify baseline attenuation value 134 for thickness 138 at location 120.

Thickness 138 may be identified in a number of different ways. For example, location 120 may be used to identify corresponding location 208 in model 210 from which an estimate of thickness 138 may be identified using geometric information 212 in model 210.

In this illustrative example, model 210 may be a model of composite structure 104. As another example, model 210 may be a model of platform 108 including composite structure 104 as shown in FIG. 1. In this illustrative example, model 210 takes the form of computer-aided design (CAD) model 214.

As depicted, geometric information 212 may be, for example, without limitation, thicknesses, lengths, orientations, and other information regarding features of composite structure 104. Corresponding location 208 in model 210 may correspond to location 120 on composite structure 104. In other words, corresponding location 208 may be a representation of location 120 on composite structure 104 in model 210.

With corresponding location 208 in model 210, analyzer 116 may identify thickness 216 for corresponding location 208 from geometric information 212 for composite structure 104 in model 210. However, thickness 216 may only be an estimate of thickness 138 for composite structure 104 at location 120. Variances may occur in thickness 138 relative to thickness 216 during manufacturing of composite structure 104. Depending on the implementation, thickness 216 may be sufficiently accurate for use by analyzer 116.

In another illustrative example, analyzer 116 may identify thickness 138 without using model 210. For example, without limitation, thicknesses 204 may be identified based on time of flight 218. Time of flight 218 may be a period of time from when sound signal 118 is sent into location 120 and response sound signal 122 is detected in FIG. 1.

With time of flight 218, analyzer 116 may identify thickness 138 using other parameters of sound signal 118. For example, the speed of sound signal 118 may be used in determining thicknesses 204 when time of flight 218 is used.

After baseline attenuation value 134 is identified, analyzer 116 may then compare baseline attenuation value 134 with attenuation 130 to generate comparison 140 in FIG. 1. With comparison 140, indication 142 may be generated indicating whether additional evaluation of location 120 is needed. In a similar fashion, analyzer 116 may identify baseline attenuation values 152 for locations 146 using database 200. Analyzer 116 may also compare attenuations 150 in FIG. 1 with baseline attenuation values 152 to form comparisons 154 and indications 156 may be generated from comparisons 154.

In these illustrative examples, analyzer 116 may generate output 220. Output 220 may be generated using at least one of comparison 140, comparisons 154, indication 142, and indications 156.

Output 220 may take a number of different forms. For example, output 220 may include map 222, report 224, alert 226, and other suitable types of output. Map 222 may be map of areas 228 on composite structure 104 in FIG. 1 that need additional evaluation based on at least one of indication 142 and indications 156. Additionally, report 224 also may include indication 142 and indications 156 as to whether additional evaluations are needed. Alert 226 may be an e-mail message, a text message, a pop-up message, or some other suitable type of alert indicating that an additional evaluation may be needed based on indication 142 and indications 156.

In this manner, output 220 in the form of at least one of map 222, report 224, alert 226, and other suitable types of outputs may assist an operator in determining which areas of composite structure 104 may need additional evaluation. As a result, ultrasound testing on composite structure 104 may be conducted efficiency and with less time-consuming data analysis. With the use of output 220, an operator may focus on areas of composite structure 104 that need additional evaluation and analysis instead of analyzing all data over the entire surface of composite structure 104 in FIG. 1.

Figure 3:
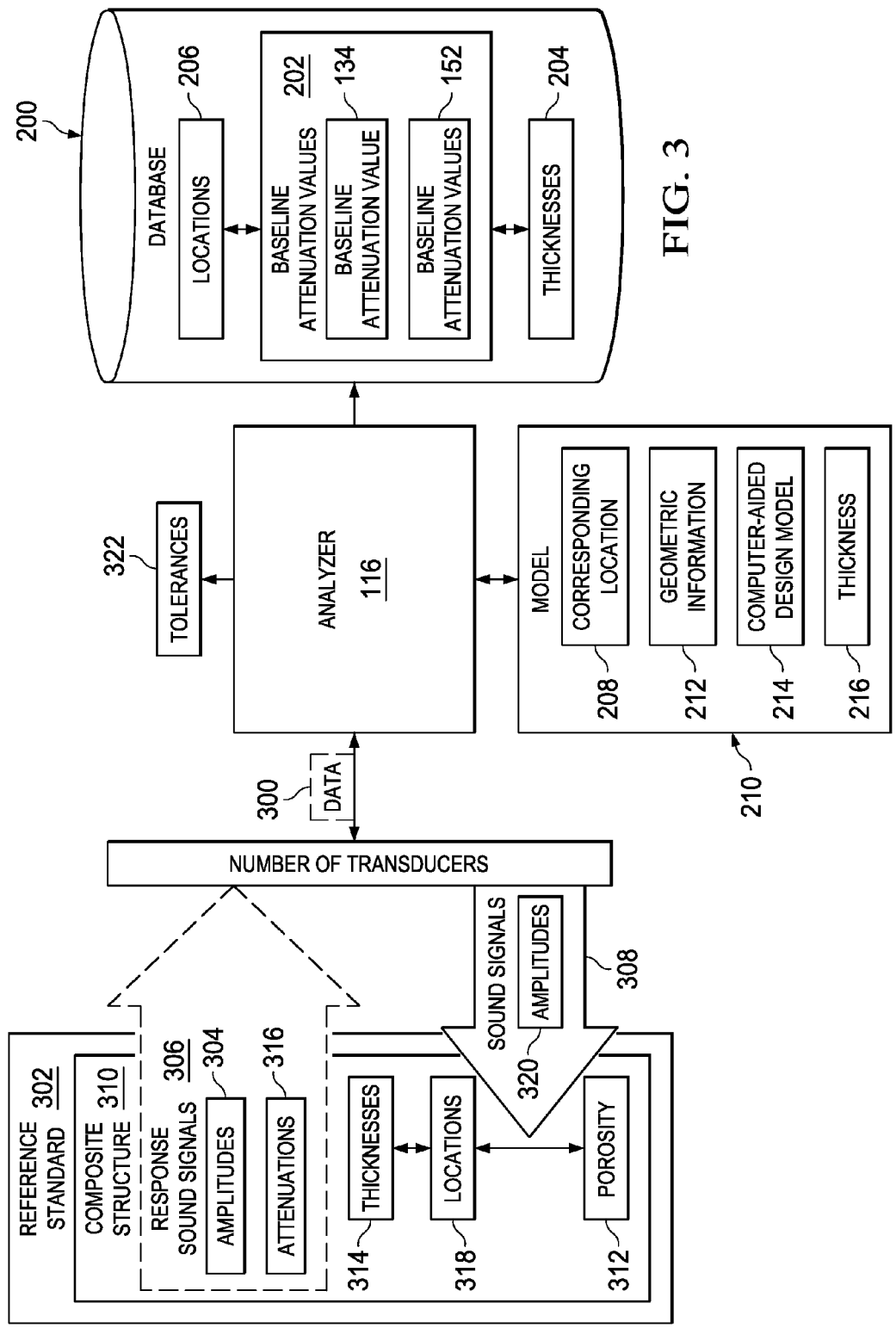
FIG. 3 is an illustration of data flow in creating baseline attenuation values in accordance with an illustrative embodiment.

Turning now to FIG. 3, an illustration of data flow in creating baseline attenuation values is depicted in accordance with an illustrative embodiment. This figure illustrates the generation of baseline attenuation values 202 for database 200.

In this illustrative example, analyzer 116 may receive data 300. Data 300 may be generated using reference standard 302. In particular, data 300 may include amplitudes 304 of response sound signals 306 generated in response to sending sound signals 308 into reference standard 302 using number of transducers 112.

Reference standard 302 may be composite structure 310. As depicted, reference standard 302 may have the same or different dimensions as composite structure 104 in FIG. 1. Reference standard 302 has porosity 312 at a desired level throughout composite structure 310 for thicknesses 314.

With amplitudes 304 in data 300, attenuations 316 in response sound signals 306 may be identified for reference standard 302 for locations 318 in reference standard 302. For example, attenuations 316 may be identified by comparing amplitudes 304 in response sound signals 306 with amplitudes 320 for sound signals 308.

In particular, attenuations 316 may be values for thicknesses 314 at locations 318 in reference standard 302. Attenuations 316 may represent values for porosity 312 in reference standard 302.

Additionally, analyzer 116 may identify tolerances 322 for porosity 312. Tolerances 322 may be based on a number of different factors. For example, tolerances 322 may be based on at least one of a desired load for reference standard 302, safety margins, and other suitable factors. With tolerances 322, attenuations 316 may be adjusted to obtain baseline attenuation values 202.

In these illustrative examples, tolerances 322 may be an allowable adjustment in porosity 312 for reference standard 302. Tolerances 322 may be the same for locations 318 or may be different for different locations in locations 318. This adjustment may be an increase in porosity 312. This adjustment may be made by increasing attenuations 316 that reflect the increase in porosity 312 that may be allowable.

As depicted, baseline attenuation values 202 in database 200 may take a number of different forms. For example, without limitation, baseline attenuation values 202 may take the form of graphs of curves, tables, length lists, flat files, and other suitable forms.

In this manner, ultrasound inspection of reference standard 302 may provide baseline attenuation values 202 for use in ultrasound inspection of composite structure 104 in FIG. 1. Further, acceptable tolerances for porosity 106 in composite structure 104 may be identified. With the identification of tolerances 322, database 200 of baseline attenuation values 202 may be generated for different thicknesses in thicknesses 204 of composite structure 104 and used for inspecting composite structure 104 in FIG. 1.

Figure 4:
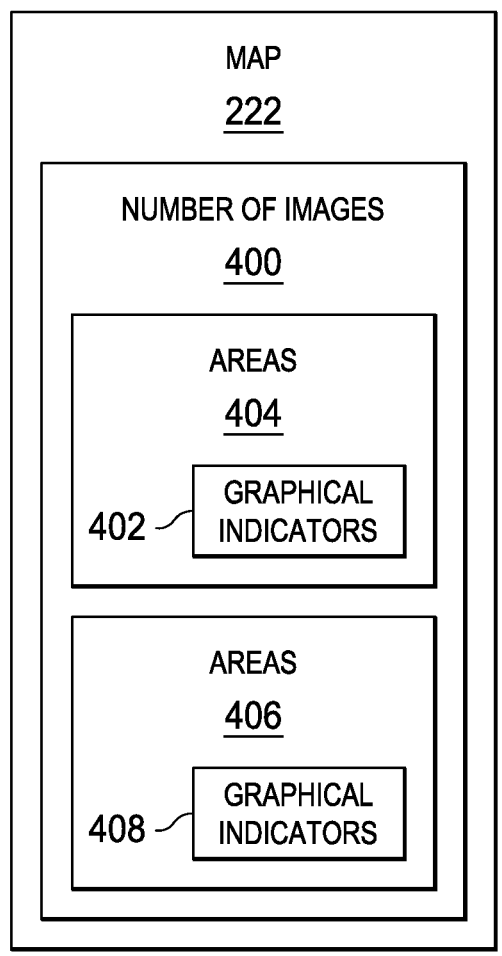
FIG. 4 is an illustration of a block diagram of a map in accordance with an illustrative embodiment.

Turning now to FIG. 4, an illustration of a block diagram of a map is depicted in accordance with an illustrative embodiment. In this illustrative example, an illustration of an implementation for map 222 in FIG. 2 is shown.

In this depicted example, map 222 may include number of images 400. Number of images 400 may be images of composite structure 104 in FIG. 1.

Additionally, graphical indicators 402 also may be present in map 222. Graphical indicators 402 may be based on indication 142 and indications 156 as generated by analyzer 116 in FIG. 1.

In particular, graphical indicators 402 may be located in areas 404 in number of images 400. Graphical indicators 402 may indicate that additional evaluations are needed for areas 404. Areas 406 without graphical indicators 402 may be areas that do not need additional evaluation. Further, graphical indicators 408 may be included in areas 406 to indicate that additional evaluations are not needed.

In these illustrative examples, graphical indicators 402 may take various forms. For example, graphical indicators 402 may be selected from at least one of a color, highlighting, bolding, text, an icon, an animation, and other suitable types of indicators. Further, graphical indicators 408 may be at least one of color, highlighting, bolding, text, an icon, an animation, and other suitable types of indicators.

The illustration of inspection environment 100 and the different components of inspection environment 100 in FIGS. 1-4 are not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, in one illustrative example, movement system 114 may be unnecessary. In still other illustrative examples, movement system 114 may be configured to move composite structure 104 in addition to or in place of moving number of transducers 112. In yet another illustrative example, movement system 114 may be a human operator that moves number of transducers 112 to location 120 and locations 146 on composite structure 104.

Although the illustrative examples for an illustrative embodiment are described with respect to platform 108 in the form of aircraft 110, an illustrative embodiment may be applied to other types of platforms. The platform may be, for example, without limitation, a mobile platform, a stationary platform, a land-based structure, an aquatic-based structure, and a space-based structure. More specifically, the platform, may be a surface ship, a tank, a personnel carrier, a train, a spacecraft, a space station, a satellite, a submarine, an automobile, a power plant, a bridge, a dam, a manufacturing facility, a building, and other suitable platforms.

In still another illustrative example, model 210 may be modified to function as database 200. Baseline attenuation values 202 may be included in model 210 in association with locations 206 in model 210. Baseline attenuation values 202 may be associated with the locations based on thicknesses in the locations in model 210.

Figure 5:
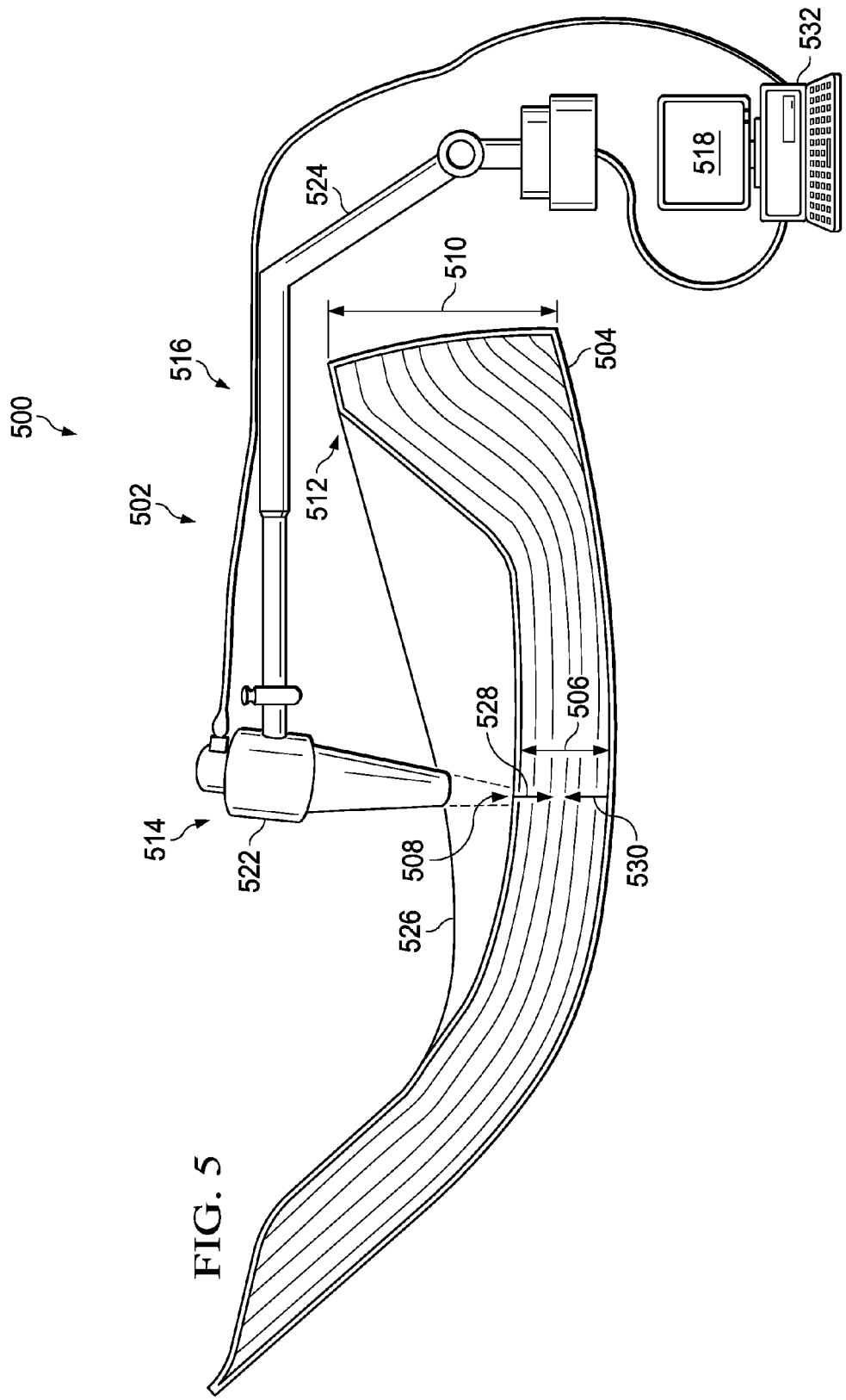
FIG. 5 is an illustration of an inspection environment in accordance with an illustrative embodiment.

Turning now to FIG. 5, an illustration of an inspection environment is depicted in accordance with an illustrative embodiment. In this depicted example, inspection environment 500 is an example of a physical implementation for inspection environment 100 and components in inspection environment 100 in FIG. 1 and FIG. 2.

In this illustrative example, inspection environment 500 includes ultrasound inspection system 502 which may be configured to inspect composite structure 504. As can be seen in this illustrative example, composite structure 504 may have thickness 506 at location 508 and thickness 510 at location 512. As can be seen, thickness 506 is different than thickness 510 in composite structure 504.

In this depicted example, ultrasound inspection system 502 may include number of transducers 514, movement system 516, and analyzer 518. As depicted, number of transducers 514 may include transducer 522. Transducer 522 may be configured to be moved by movement system 516.

In this example, movement system 516 may include robotic arm 524. Robotic arm 524 may be configured to be controlled by analyzer 518. In this illustrative example, robotic arm 524 may be configured to move transducer 522 to different locations on surface 526 of composite structure 504.

In this illustrative example, transducer 522 may be configured to send sound signal 528 into composite structure 504 at location 508. Additionally, transducer 522 may also be configured to detect response sound signal 530. Transducer 522 generates data and sends the data to analyzer 518 in response to detecting response sound signal 530.

In this illustrative example, analyzer 518 may be implemented in computer 532. Computer 532 may be one implementation for a computer in computer system 128 shown in block form in FIG. 1. Analyzer 518 may identify the attenuation for response sound signal 530 and determine whether an indication should be generated for location 508. This determination may be based on a desired level of porosity for thickness 506 at location 508. The attenuation may be used to identify the amount of porosity based on thickness 506 at location 508.

In these illustrative examples, transducer 522 may be moved by robotic arm 524 to other locations on surface 526 of composite structure 504 to send additional sound signals and detect additional response sound signals. This information from other locations may be used to generate indications of whether additional evaluation is needed for those locations.

Figure 6:
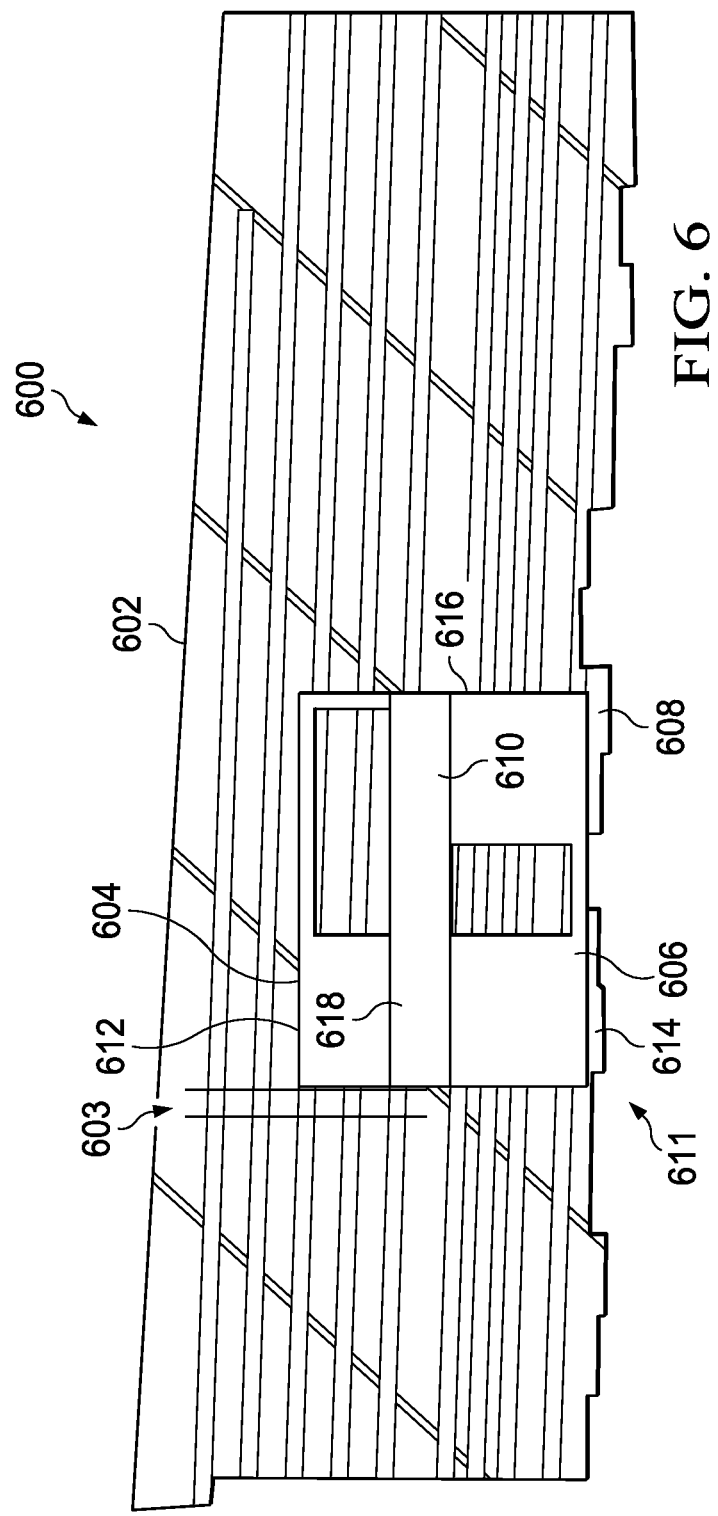
FIG. 6 is an illustration of a map in accordance with an illustrative embodiment.

Turning now to FIG. 6, an illustration of a map is depicted in accordance with an illustrative embodiment. In this depicted example, map 600 is an example of an implementation for map 222 shown in block form in FIG. 2. In this illustrative example, map 600 may be generated by analyzer 116 as part of output 220 in FIG. 2.

As depicted, map 600 is comprised of image 602 and graphical indicators 603. As illustrated, graphical indicators 603 may include graphical indicator 604, graphical indicator 606, graphical indicator 608, and graphical indicator 610.

As illustrated, graphical indicators 603 may be located in areas 611. Areas 611 include area 612, area 614, area 616, and area 618.

In particular, graphical indicator 604 is located in area 612. Graphical indicator 606 may be located in area 614. Graphical indicator 608 may be located in area 616. Graphical indicator 610 may be located in area 618.

Graphical indicator 604, graphical indicator 606, and graphical indicator 608 may indicate that an additional evaluation is needed for area 612, area 614, and area 616, respectively. In this particular illustrative example, graphical indicator 610 may indicate that area 618 is a "no-test" area.

A no-test area may be a location on composite structure 104 in FIG. 1 that may have no inspection requirement or criteria. A location may not have an inspection requirement because erroneous data may be generated when that location is inspected. For example, a no-test area may be a location on composite structure 104 where a taper is present. A taper in composite structure 104 may scatter sound signal 118 when ultrasound inspection system 102 is used to inspect the composite structure in FIG. 1. This scatter may result in inaccurate attenuations 150 in FIG. 1. Thus, when determining the attenuation over a larger area, no-test areas may not be included in the data, analysis, or both.

In other illustrative examples, a no-test area may be present in a portion of composite structure 104 in FIG. 1. In this example, the no-test area may contain a foam core. This foam core may be embedded between layers of composite structure 104. In this instance, the foam core may scatter or absorb sound that may result in inaccurate attenuations 150 in FIG. 1. In still other illustrative examples, a foaming adhesive may be used in composite structure 104. This foaming adhesive may also result in a no-test area. Of course, other materials within composite structure 104 may result in no-test areas.

When analyzing the test data, analyzer 116 in FIG. 1 may take into account these no-test areas. For example, analyzer 116 may normalize the test data by removing the results of the no-test area from attenuations 150 for composite structure 104 in FIG. 1.

Figure 7:
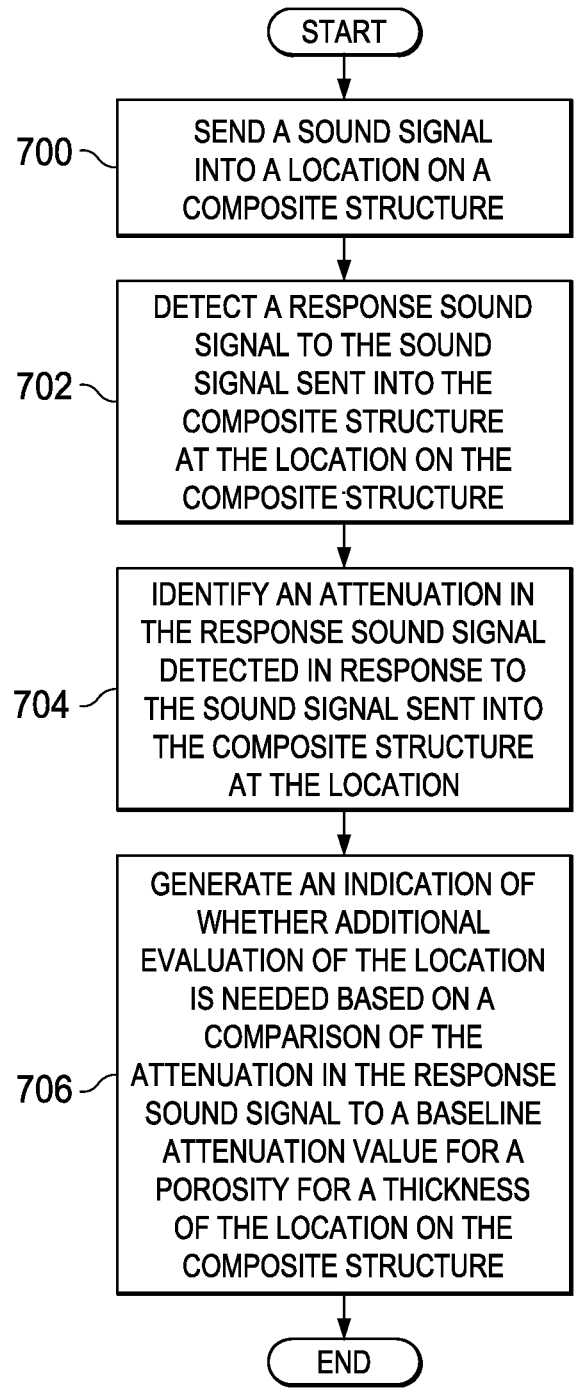
FIG. 7 is an illustration of a flowchart of a process for detecting attenuation in composite structures in accordance with an illustrative embodiment.

Turning now to FIG. 7, an illustration of a flowchart of a process for detecting attenuation in composite structures is depicted in accordance with an illustrative embodiment. The process illustrated in FIG. 7 may be implemented in inspection environment 100 in FIG. 1. In particular, the process may be implemented by ultrasound inspection system 102 to inspect composite structure 104 in FIG. 1.

The process may begin by sending sound signal 118 into composite structure 104 at location 120 (operation 700). The process may then detect response sound signal 122 to sound signal 118 sent into composite structure 104 at location 120 on composite structure 104 (operation 702).

Attenuation 130 may be identified in response sound signal 122 detected in response to sound signal 118 sent into composite structure 104 at location 120 (operation 704). Thereafter, indication 142 of whether additional evaluation of location 120 is needed based on comparison 140 of attenuation 130 in response sound signal 122 to baseline attenuation value 134 for porosity 106 for thickness 138 of location 120 on composite structure 104 may be generated (operation 706) with the process terminating thereafter.

The different operations illustrated in FIG. 7 may be performed for any number of locations on composite structure 104. The identification of attenuations and the generation of indications may be performed each time a response sound signal is detected. Alternatively, these operations may performed after sound signals have been sent into all the locations and response sound signals have been detected for these locations.

Figure 8:
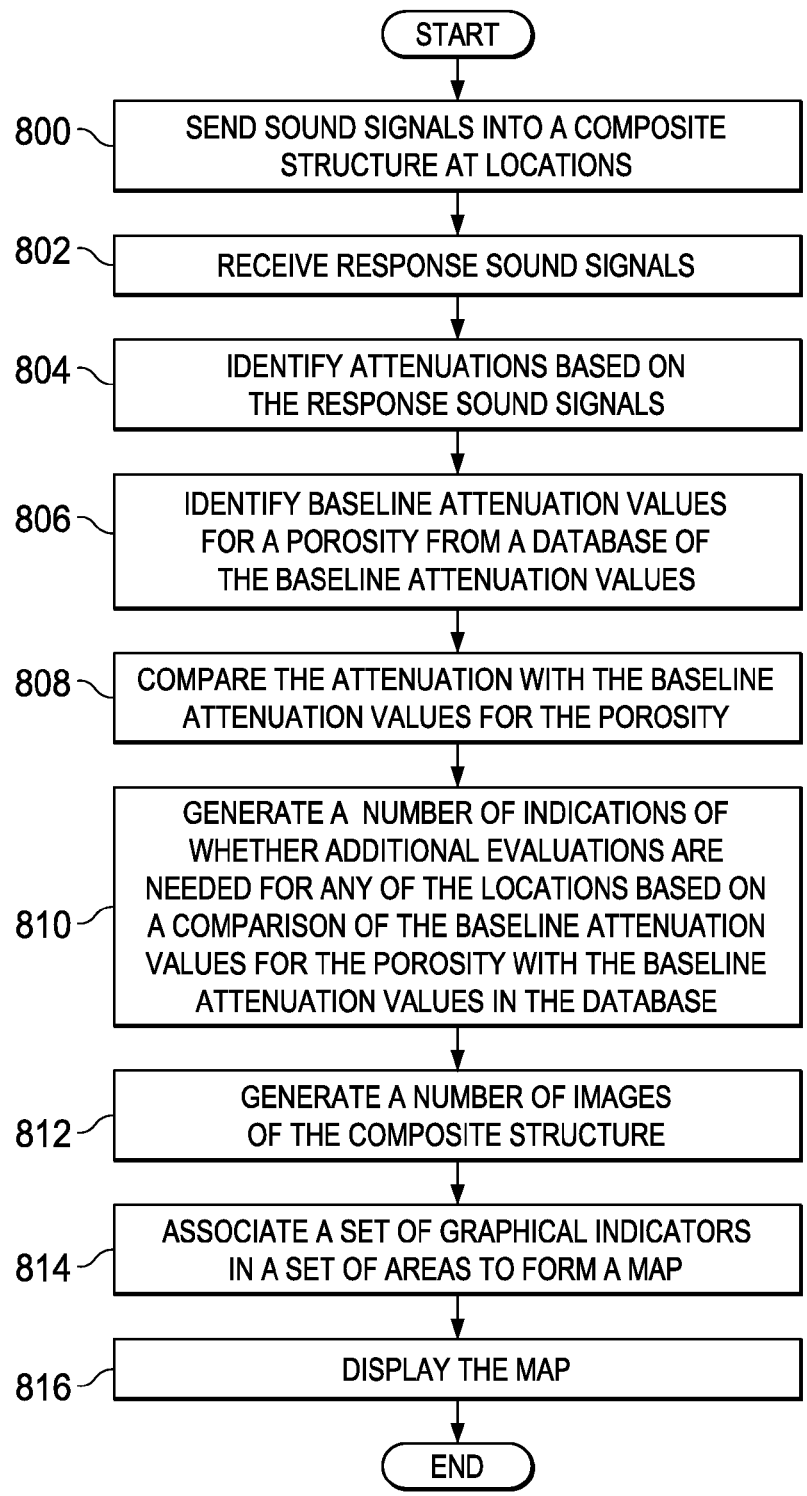
FIG. 8 is an illustration of a flowchart of a process for inspecting a composite structure in accordance with an illustrative embodiment.

Turning now to FIG. 8, an illustration of a flowchart of a process for inspecting a composite structure is depicted in accordance with an illustrative embodiment. The process illustrated in FIG. 8 may be implemented in inspection environment 100 in FIG. 1. In particular, the process may be implemented using ultrasound inspection system 102 to inspect composite structure 104 in FIG. 1.

The process may begin by sending sound signals 144 into composite structure 104 at locations 146 (operation 800). The process then receives response sound signals 148 (operation 802). The process may then identify attenuations 150 based on response sound signals 148 (operation 804). The process may then identify baseline attenuation values 152 for porosity 106 from database 200 of baseline attenuation values 202 (operation 806).

The process may then compare attenuations 150 with baseline attenuation values 152 for porosity 106 (operation 808). The process may then generate a number of indications of whether additional evaluations are needed for any of locations 146 based on comparisons 154 of baseline attenuation values 152 for porosity 106 with baseline attenuation values 202 in database 200 (operation 810). An indication may indicate either an additional evaluation is needed or that an additional evaluation is not needed, depending on the particular implementation. In some cases, only an indication that an additional evaluation is needed may be generated when generating the number of indications.

The process may generate a number of images of composite structure 104 (operation 812). Next, the process may associate a set of graphical indicators in a set of areas to form a map (operation 814). A "set," as used herein, may be zero or more items. For example, a set of graphical indicators may be zero or more graphical indicators. In other words, if the number of indications do not indicate that an additional evaluation is needed, then graphical indicators are not generated for the set of graphical indicators. Thus, the set of graphical indicators would be a null set.

The process then displays the map (operation 816) with the process terminating thereafter. The map may be used by an operator to perform additional evaluations if needed based on the results displayed using the set of graphical indicators on the map.

Figure 9:
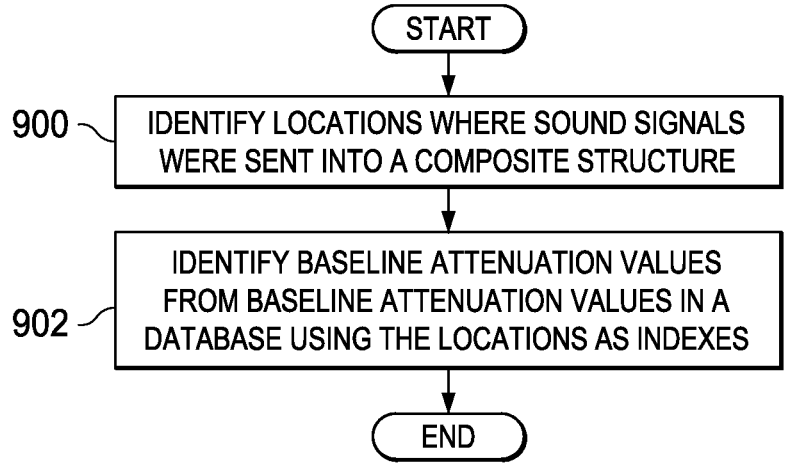
FIG. 9 is an illustration of a flowchart of a process for inspecting a composite structure in accordance with an illustrative embodiment.

Turning now to FIG. 9, an illustration of a flowchart of a process identifying baseline attenuation values from a database of baseline attenuation values is depicted in accordance with an illustrative embodiment. The process illustrated in FIG. 9 is an example of one implementation for operation 806 in FIG. 8.

The process may begin by identifying locations 146 where sound signals 144 were sent into composite structure 104 (operation 900). The process may then identify baseline attenuation values 152 from baseline attenuation values 202 in database 200 using locations 146 as indexes (operation 902) with the process terminating thereafter.

Figure 10:
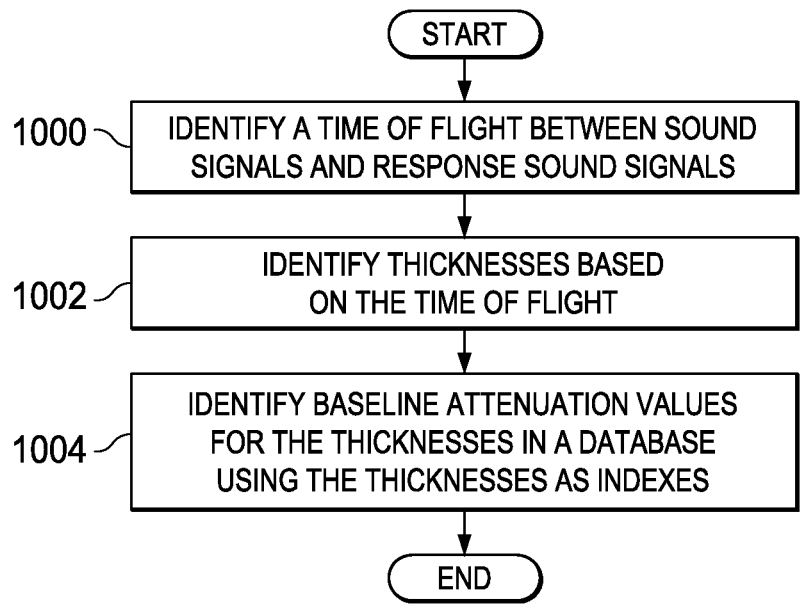
FIG. 10 is an illustration of a flowchart of a process for identifying baseline attenuation values from a database of baseline attenuation values in accordance with an illustrative embodiment.

Turning now to FIG. 10, an illustration of a flowchart of a process for identifying baseline attenuation values from a database of baseline attenuation values is depicted in accordance with an illustrative embodiment. The process illustrated in FIG. 10 is an example of another implementation for operation 806 in FIG. 8.

The process begins by identifying time of flight 218 between sound signals 144 and response sound signals 148 (operation 1000). Time of flight 218 may be a period of time from when sound signals 144 are sent into locations 146 and response sound signals 148 are detected. Next, the process may identify thicknesses 204 based on time of flight 218 (operation 1002). The process may then identify baseline attenuation values 202 for thicknesses 204 in database 200 using thicknesses 204 as indexes (operation 1004) with the process terminating thereafter.

Figure 11:
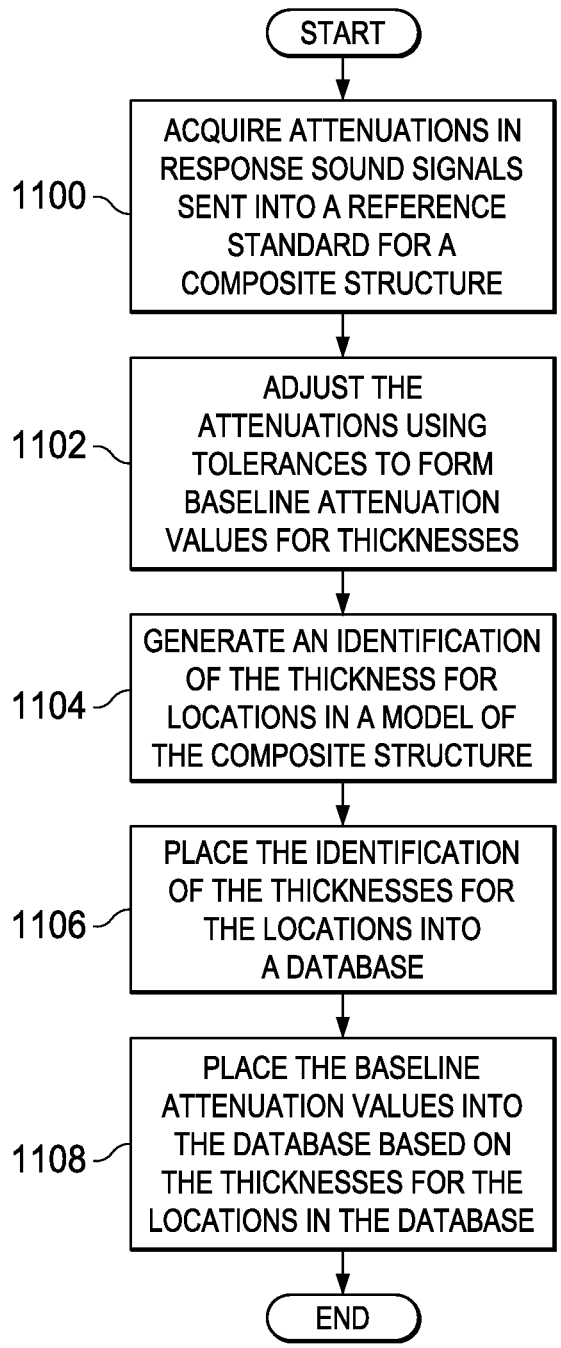
FIG. 11 is an illustration of a flowchart of a process for generating baseline attenuation values in accordance with an illustrative embodiment.

Turning now to FIG. 11, an illustration of a flowchart of a process for generating baseline attenuation values is depicted in accordance with an illustrative embodiment. The process illustrated in FIG. 11 may be used to generate baseline attenuation values 202 in database 200 in FIG. 2.

The process may begin by acquiring attenuations 316 in response signals generated in response to sound signals sent into reference standard 302 for composite structure 104 (operation 1100). In these illustrative examples, attenuations 316 may be obtained for different thicknesses 314 in reference standard 302. Reference standard 302 for composite structure 104 may have the desired level of porosity 312 for different thicknesses 314 in reference standard 302. Thereafter, attenuations 316 may be adjusted using tolerances 322 to form baseline attenuation values 202 for thicknesses 314 (operation 1102).

Next, an identification of thicknesses 314 for locations 318 in model 210 of composite structure 310 may be generated (operation 1104). In other words, a thickness may be identified for every location in model 210. The identification of thicknesses 314 for locations 318 may be placed into database 200 (operation 1106). The placement of thicknesses 314 for locations 318 may form thicknesses 204 for locations 206 in database 200.

Baseline attenuation values 202 may then be placed into database 200 based on thicknesses 314 for locations 318 in database 200 (operation 1108) with the process terminating thereafter. In other words, a baseline attenuation value for a particular thickness in baseline attenuation values 202 may be associated with every location that has the same thickness in database 200.

In this manner, database 200 may form a thickness map database that identifies the thickness of composite structure 104 for every location in locations 206 as identified from model 210. In this manner, a location in composite structure 104 may be used as an index to identify a baseline attenuation value from baseline attenuation values 202 in database 200.

In some illustrative examples, baseline attenuation values 202 in database 200 do not need to be associated with locations 206. Instead, baseline attenuation values 202 may only be associated with thicknesses 204. This organization of baseline attenuation values 202 may be used when a thickness of composite structure 104 is used as an index to baseline attenuation values 202 instead of a location of composite structure 104.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

For example, in FIG. 8, data is received for all of the response sound signals in operation 804 before identifying attenuations for the response sound signals and comparing the attenuations to baseline attenuation values to generate the number of indications. This type of processing may be referred to as a post-processing of data. In other illustrative examples, the operations may be performed each time a response sound signal is received rather than after all of the response sound signals have been received. This type of processing may be referred to as dynamic processing of data.

Figure 12:
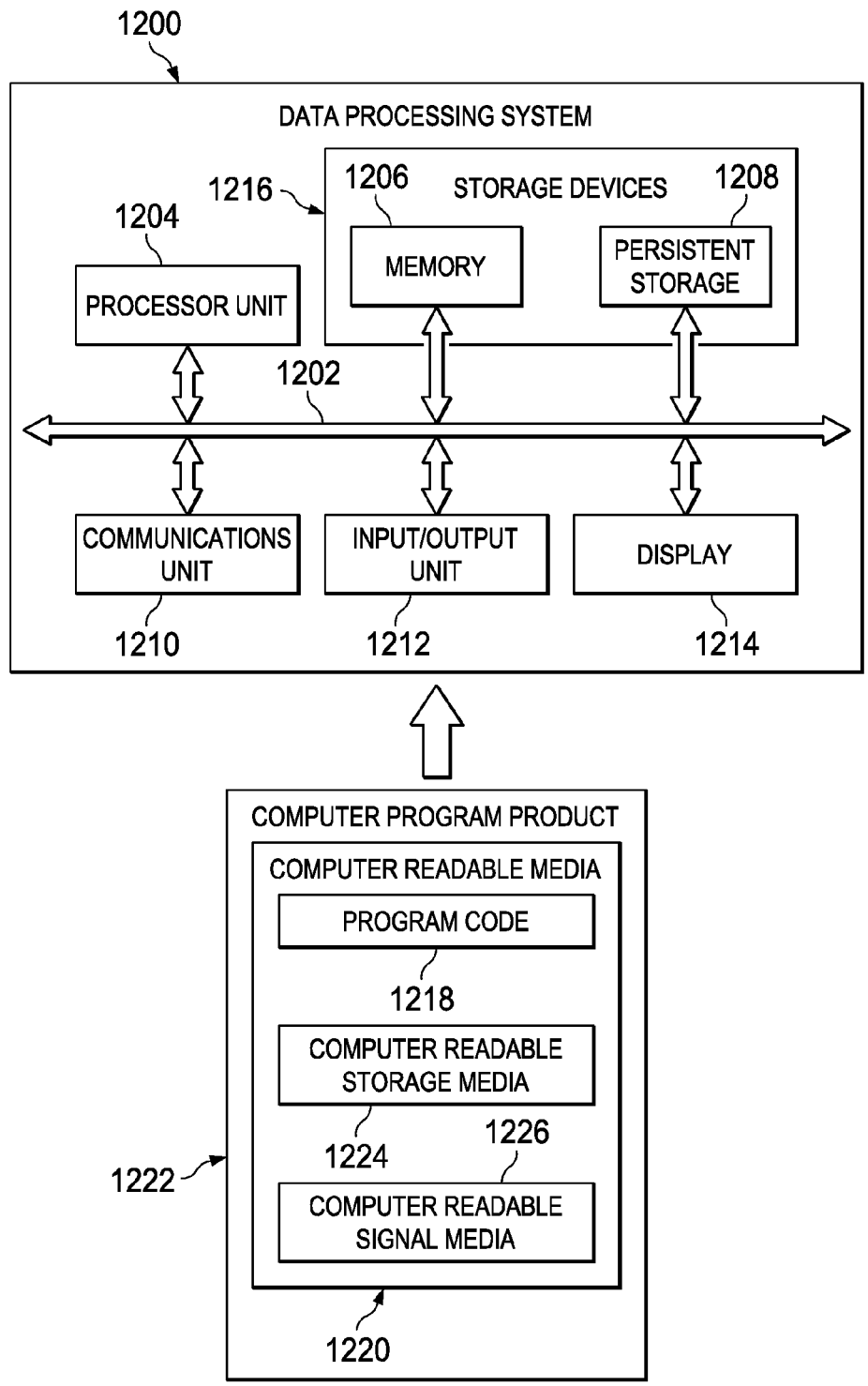
FIG. 12 is an illustration of a data processing system in accordance with an illustrative embodiment.

Turning now to FIG. 12, an illustration of a data processing system is depicted in accordance with an illustrative embodiment. Data processing system 1200 may be used to implement one or more computers in computer system 128 in FIG. 1. In this illustrative example, data processing system 1200 includes communications framework 1202, which may provide communications between processor unit 1204, memory 1206, persistent storage 1208, communications unit 1210, input/output (I/O) unit 1212, and display 1214. In this example, communication framework may take the form of a bus system.

Processor unit 1204 may execute instructions for software that may be loaded into memory 1206. Processor unit 1204 may be a number of processors, a multi-processor core, or some other type of processor, depending on the particular implementation.

Memory 1206 and persistent storage 1208 may be examples of storage devices 1216. A storage device may be any piece of hardware that is capable of storing information, such as, for example, without limitation, data, program code in functional form, and/or other suitable information either on a temporary basis and/or a permanent basis. Storage devices 1216 may also be referred to as computer readable storage devices in these illustrative examples. Memory 1206, in these examples, may be, for example, a random access memory or any other suitable volatile or non-volatile storage device. Persistent storage 1208 may take various forms, depending on the particular implementation.

For example, persistent storage 1208 may contain one or more components or devices. For example, persistent storage 1208 may be a hard drive, a flash memory, a rewritable optical disk, a rewritable magnetic tape, or some combination of the above. The media used by persistent storage 1208 also may be removable. For example, a removable hard drive may be used for persistent storage 1208.

Communications unit 1210, in these illustrative examples, may provide for communications with other data processing systems or devices. In these illustrative examples, communications unit 1210 may be a network interface card.

Input/output (I/O) unit 1212 may allow for input and output of data with other devices that may be connected to data processing system 1200. For example, input/output (I/O) 1212 may provide a connection for user input through a keyboard, a mouse, and/or some other suitable input device. Further, input/output (I/O) unit 1212 may send output to a printer. Display 1214 provides a mechanism to display information to a user.

Instructions for the operating system, applications, and/or programs may be located in storage devices 1216, which are in communication with processor unit 1204 through communications framework 1202. The processes of the different embodiments may be performed by processor unit 1204 using computer-implemented instructions, which may be located in a memory, such as memory 1206.

These instructions may be referred to as program code, computer usable program code, or computer readable program code that may be read and executed by a processor in processor unit 1204. The program code in the different embodiments may be embodied on different physical or computer readable storage media, such as memory 1206 or persistent storage 1208.

Program code 1218 may be located in a functional form on computer readable media 1220 that is selectively removable and may be loaded onto or transferred to data processing system 1200 for execution by processor unit 1204. Program code 1218 and computer readable media 1220 may form computer program product 1222 in these illustrative examples. In one example, computer readable media 1220 may be computer readable storage media 1224 or computer readable signal media 1226.

In these illustrative examples, computer readable storage media 1224 is a physical or tangible storage device used to store program code 1218 rather than a medium that propagates or transmits program code 1218.

Alternatively, program code 1218 may be transferred to data processing system 1200 using computer readable signal media 1226. Computer readable signal media 1226 may be, for example, a propagated data signal containing program code 1218. For example, computer readable signal media 1226 may be an electromagnetic signal, an optical signal, and/or any other suitable type of signal. These signals may be transmitted over communications links, such as wireless communications links, optical fiber cable, coaxial cable, a wire, and/or any other suitable type of communications link.

The different components illustrated for data processing system 1200 are not meant to provide architectural limitations to the manner in which different embodiments may be implemented. The different illustrative embodiments may be implemented in a data processing system including components in addition to and/or in place of those illustrated for data processing system 1200. Other components shown in FIG. 12 can be varied from the illustrative examples shown. The different embodiments may be implemented using any hardware device or system capable of running program code 1218.

Figure 13:
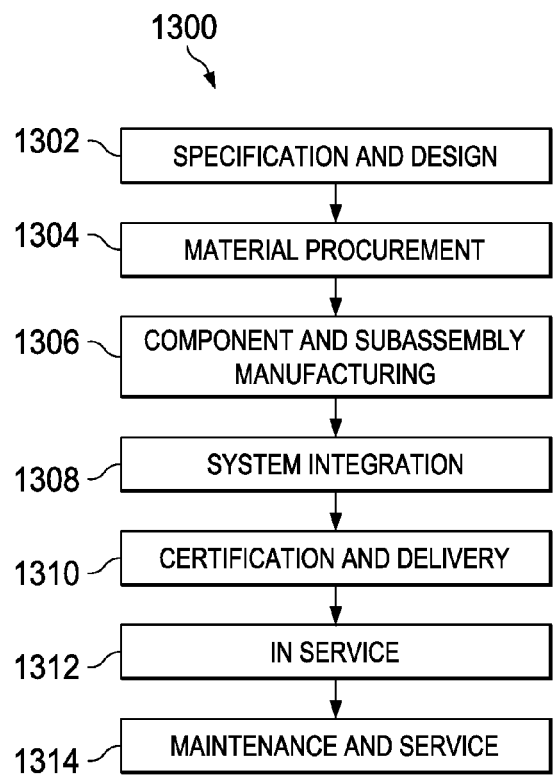
FIG. 13 is an illustration of an aircraft manufacturing and service method in accordance with an illustrative embodiment.
Figure 14:
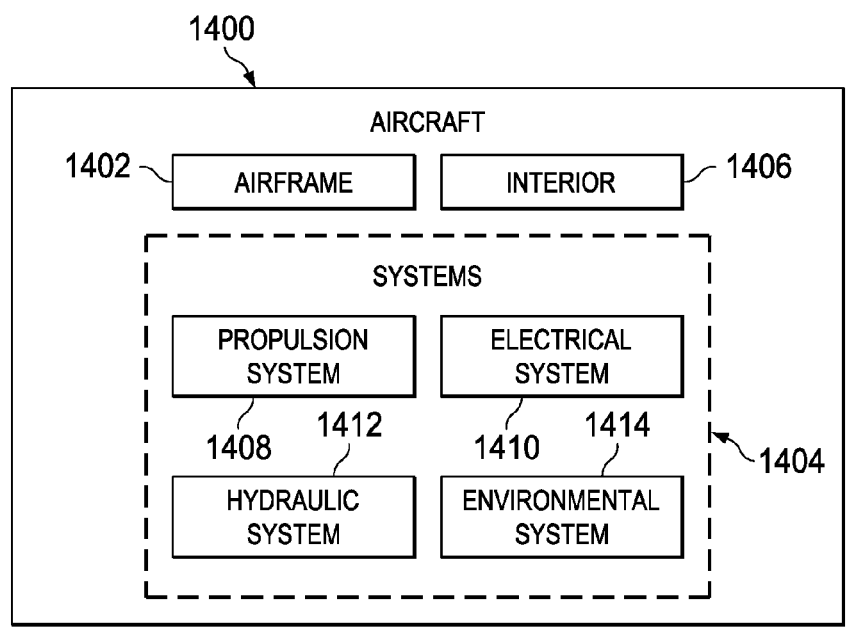
FIG. 14 is an illustration of an aircraft in which an illustrative embodiment may be implemented.

Illustrative embodiments of the disclosure may be described in the context of aircraft manufacturing and service method 1300 as shown in FIG. 13 and aircraft 1400 as shown in FIG. 14. For example, ultrasound inspection system 102 may be used during at least one of the steps shown in this figure.

Turning first to FIG. 13, an illustration of an aircraft manufacturing and service method is depicted in accordance with an illustrative embodiment. During pre-production, aircraft manufacturing and service method 1300 may include specification and design 1302 of aircraft 1400 in FIG. 14 and material procurement 1304.

During production, component and subassembly manufacturing 1306 and system integration 1308 of aircraft 1400 in FIG. 14 takes place. Thereafter, aircraft 1400 in FIG. 14 may go through certification and delivery 1310 in order to be placed in service 1312. While in service 1312 by a customer, aircraft 1400 in FIG. 14 is scheduled for routine maintenance and service 1314, which may include modification, reconfiguration, refurbishment, and other maintenance or service.

Each of the processes of aircraft manufacturing and service method 1300 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 14, an illustration of an aircraft is depicted in which an illustrative embodiment may be implemented. Aircraft 1400 may be one implementation for platform 108 in FIG. 1. Specifically, aircraft 1400 may be one implementation for aircraft 110 in FIG. 1.

In this example, aircraft 1400 is produced by aircraft manufacturing and service method 1300 in FIG. 13 and may include airframe 1402 with plurality of systems 1404 and interior 1406. Examples of systems 1404 include one or more of propulsion system 1408, electrical system 1410, hydraulic system 1412, and environmental system 1414. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1300 in FIG. 13. In one illustrative example, composite structures manufactured during component and subassembly manufacturing 1306 may be inspected using ultrasound inspection system 102 as well as composites that may be manufactured while aircraft 1400 is in service 1312 or during maintenance and service 1314. One or more apparatus embodiments, method embodiments, or a combination thereof may be utilized while aircraft 1400 is in service 1312 and/or during maintenance and service 1314 in FIG. 13. The use of a number of the different illustrative embodiments may substantially expedite the assembly of and/or reduce the cost of aircraft 1400.

Thus, the illustrative embodiments provide a method and apparatus for inspecting composite structures. By using ultrasound inspection system 102, inspections of composite structures may be made more quickly and with less effort from operators. Ultrasound inspection system 102 is configured to provide indications of whether additional evaluations are needed by an operator. These indications may be based on a comparison of the attenuation in response sound signals to baseline attenuation values. These baseline attenuation values may be selected to provide an indication of when the porosity is greater than a desired level. Thus, when the attenuation is greater than a baseline attenuation value, additional evaluation of the location may be needed.

In these illustrative examples, the indications may be provided in an output such as a map. The map allows for an operator to quickly identify whether an area of the composite structure needs additional evaluation and what areas may need additional evaluations. As a result, the operator may not need to review all of the data to determine whether additional evaluations may be needed.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for inspecting a composite structure, the method comprising:
    detecting a response sound signal to a sound signal sent into the composite structure at a location on the composite structure;
    identifying an attenuation in the response sound signal detected in response to the sound signal sent into the composite structure at the location on the composite structure;
    generating an indication of whether additional evaluation of the location is needed based on a comparison of the attenuation in the response sound signal to a baseline attenuation value for porosity for the location on the composite structure;
    generating a number of images of the composite structure; and
    associating a set of graphical indicators on the number of images in areas corresponding to a set of areas on the composite structure needing the additional evaluation using the number of indications to form a map of areas on the composite structure needing additional evaluation using the number of indications.

2. The method of claim 1 further comprising:
    sending the sound signal into the composite structure at the location on the composite structure.

3. The method of claim 1, wherein the detecting step, the identifying step, and the generating step are performed for locations on the composite structure to generate a number of indications of whether additional evaluation of the locations is needed.

4. The method of claim 1 further comprising:
    identifying the baseline attenuation value for porosity at the location on the composite structure; and
    comparing the attenuation of the response sound signal with the baseline attenuation value for porosity for the location on the composite structure to form the comparison.

5. The method of claim 4, wherein identifying the baseline attenuation value for porosity at the location on the composite structure comprises:
    identifying a corresponding location in a model of the composite structure that corresponds to the location on the composite structure; and
    identifying the baseline attenuation value for porosity assigned to the corresponding location in the model.

6. The method of claim 4, wherein identifying the baseline attenuation value for porosity at the location on the composite structure comprises:
    identifying the baseline attenuation value for porosity from a database of baseline attenuation values for locations on the composite structure.

7. The method of claim 4, wherein identifying the baseline attenuation value for porosity at the location on the composite structure comprises:
    identifying the baseline attenuation value for porosity from a database of baseline attenuation values for thicknesses in the composite structure using a thickness of the composite structure at the location.

8. The method of claim 7 further comprising:
    identifying the thickness of the composite structure at the location using a model of the composite structure.

9. The method of claim 7 further comprising:
    identifying the thickness of the composite structure at the location from a time of flight between the sound signal and the response sound signal.

10. The method of claim 1, wherein the composite structure is selected from one of a skin panel, a fuselage barrel, a stringer, a panel, a flap, a door, and a wing box.

11. A method for inspecting a composite structure comprising:
    sending a sound signal into the composite structure at a location on the composite structure;
    detecting a response sound signal to the sound signal sent into the composite structure at the location on the composite structure;
    identifying an attenuation in the response sound signal detected in response to the sound signal sent into the composite structure at the location on the composite structure;
    identifying a baseline attenuation value for porosity at the location on the composite structure;
    comparing the attenuation of the response sound signal with the baseline attenuation value for porosity for the location on the composite structure to form a comparison;
    generating an indication of whether additional evaluation of the location is needed based on the comparison of the attenuation in the response sound signal to the baseline attenuation value for porosity for the location on the composite structure, wherein the sending step, the detecting step, the identifying steps, and the generating step are performed for locations on the composite structure to form a number of indications of whether additional evaluation of the locations is needed;
    generating a number of images of the composite structure; and
    associating a set of graphical indicators on the number of images in areas corresponding to a set of areas on the composite structure needing the additional evaluation using the number of indications to form a map of areas on the composite structure needing additional evaluation using the number of indications.

12. The method of claim 11, wherein identifying the baseline attenuation value for porosity at the location on the composite structure comprises:
identifying a corresponding location in a model of the composite structure that corresponds to the location on the composite structure; and
identifying the baseline attenuation value for porosity assigned to the corresponding location in the model.

13. The method of claim 11, wherein identifying the baseline attenuation value for porosity at the location on the composite structure comprises:
identifying the baseline attenuation value for porosity from a database of baseline attenuation values for locations on the composite structure.

14. The method of claim 11, wherein identifying the baseline attenuation value for porosity at the location on the composite structure comprises:
identifying a thickness of the composite structure at the location using at least one of a model of the composite structure and a time of flight between the sound signal and the response sound signal; and
identifying the baseline attenuation value for porosity from a database of baseline attenuation values for thicknesses in the composite structure using the thickness of the composite structure at the location.

15. The method of claim 11, wherein the composite structure is selected from one of a skin panel, a fuselage barrel, a stringer, a panel, a flap, a door, and a wing box.

16. An apparatus comprising:
a number of transducers configured to send sound signals into the composite structure and detect response sound signals to the sound signals sent into the composite structure; and
an analyzer configured to
identify an attenuation in a response sound signal detected in response to a sound signal sent into a composite structure at a location;
generate an indication of whether additional evaluation of the location is needed based on a comparison of the attenuation in the response sound signal to a baseline attenuation value for porosity for the location on the composite structure;
generate a number of images of the composite structure; and
associate a set of graphical indicators on the number of images in areas corresponding to a set of areas on the composite structure needing the additional evaluations using the number of indications to form a map of areas on the composite structure needing the additional evaluations using the number of indications.

17. The apparatus of claim 16, wherein the analyzer is further configured to send the sound signal into the location on the composite structure.

18. The apparatus of claim 16, wherein the analyzer is further configured to detect the response sound signal to the sound signal sent into the composite structure at the location on the composite structure; identify the attenuation in the response sound signal detected in response to the sound signal sent into the composite structure at the location; and generate the indication of whether additional evaluation of the location is needed based on the comparison of the attenuation in the response sound signal to the baseline attenuation value for porosity for the location on the composite structure for locations on the composite structure to generate a number of indications of whether additional evaluation of the locations is needed.

19. The apparatus of claim 16, wherein the analyzer is further configured to identify the baseline attenuation value for porosity at the location on the composite structure and compare the attenuation of the response sound signal with the baseline attenuation value for porosity for the location on the composite structure to form the comparison.

20. The apparatus of claim 19, wherein in being configured to identify the baseline attenuation value for porosity at the location on the composite structure, the analyzer is further configured to identify a corresponding location in a model of the composite structure that corresponds to the location on the composite structure and identify the baseline attenuation value for porosity assigned to the corresponding location in the model.

21. The apparatus of claim 19, wherein in being configured to identify the baseline attenuation value at the location in the composite structure, the analyzer is further configured to identify the baseline attenuation value for porosity from a database of baseline attenuation values for locations on the composite structure.

22. The apparatus of claim 19, wherein in being configured to identify the baseline attenuation value for porosity at the location in the composite structure, the analyzer is configured to identify the baseline attenuation value for porosity from a database of baseline attenuation values for thicknesses in the composite structure using a thickness of the composite structure at the location.

23. The apparatus of claim 22, wherein the analyzer is further configured to identify the thickness at the location using a model of the composite structure.

24. The apparatus of claim 22, wherein the analyzer is further configured to identify the thickness of the composite structure at the location from a time of flight between the sound signal and the response sound signal.

25. The apparatus of claim 16, wherein the composite structure is selected from one of a skin panel, a fuselage barrel, a stringer, a panel, a flap, a door, and a wing box.

26. An ultrasound inspection system for a composite structure, the ultrasound inspection system comprising:
a number of transducers configured to send sound signals into the composite structure and detect response sound signals to the sound signals sent into the composite structure; and
an analyzer configured to
detect the response sound signals to the sound signals sent into the composite structure at locations on the composite structure;
identify attenuations in the response sound signals detected in response to the sound signals sent into the composite structure at the locations;
identify baseline attenuation values for porosity at the locations on the composite structure;
compare the attenuations of the response sound signals with the baseline attenuation values for porosity for the locations on the composite structure to form comparisons;
generate a number of indications of whether additional evaluations of the locations are needed based on the comparisons of the attenuations in the response sound signals to the baseline attenuation values for porosity for the locations on the composite structure;
generate a number of images of the composite structure; and associate a set of graphical indicators on the number of images in areas corresponding to a set of areas on the composite structure needing the additional evaluations using the number of indications to form a map of areas on the composite structure needing the additional evaluations using the number of indications.

27. The ultrasound inspection system of claim 26, wherein in being configured to identify the baseline attenuation values for porosity at the locations on the composite structure, the analyzer is configured to identifying corresponding locations in a model of the composite structure that correspond to the locations on the composite structure and identify the baseline attenuation values for porosity assigned to the locations in the model.

28. The ultrasound inspection system of claim 26, wherein in being configured to identify the baseline attenuation values for porosity at the locations in the composite structure, the analyzer is configured to identify the baseline attenuation values for porosity from a database of baseline attenuation values for the locations on the composite structure.

29. The ultrasound inspection system of claim 26, wherein in being configured to identify the baseline attenuation values for porosity at the locations in the composite structure, the analyzer is configured to identify thicknesses at the locations using at least one of a model of the composite structure and times of flight between the sound signals and the response sound signals and identify the baseline attenuation values for porosity from a database of baseline attenuation values for the thicknesses in the composite structure using a thickness of the composite structure at the locations.

* * * * *